United States Patent
Feenstra et al.

(10) Patent No.: US 6,828,325 B2
(45) Date of Patent: Dec. 7, 2004

(54) PHENYLPIPERAZINES

(75) Inventors: Roelof W. Feenstra, Weesp (NL); Eric Ronken, Weesp (NL); Cornelis G. Kruse, Weesp (NL); Andrew C. McCreary, Weesp (NL); Gustaaf J. M. van Scharrenburg, Weesp (NL)

(73) Assignee: Solvay Pharmaceuticals B.V., Weesp (CH)

( * ) Notice: Subject to any disclaimer, the term of this patent is extended or adjusted under 35 U.S.C. 154(b) by 0 days.

(21) Appl. No.: 10/343,232

(22) PCT Filed: Feb. 19, 2002

(86) PCT No.: PCT/EP02/01793

§ 371 (c)(1),
(2), (4) Date: Jan. 30, 2003

(87) PCT Pub. No.: WO02/066472

PCT Pub. Date: Aug. 29, 2002

(65) Prior Publication Data

US 2003/0162791 A1 Aug. 28, 2003

(30) Foreign Application Priority Data

Feb. 21, 2001 (EP) .............................................. 01200609

(51) Int. Cl.[7] ..................... A61K 31/496; C07D 413/14
(52) U.S. Cl. .................... 514/254.02; 544/368
(58) Field of Search ...................... 544/368; 514/254.02

(56) References Cited

FOREIGN PATENT DOCUMENTS

| | | |
|---|---|---|
| EP | 0 900 792 A | 3/1999 |
| WO | WO 99 67237 | 12/1999 |
| WO | WO 00 23441 | 4/2000 |
| WO | 01/14330 A2 * | 3/2001 |
| WO | 03/068207 A2 * | 8/2003 |

OTHER PUBLICATIONS

Robichaud et al, Annual Reports in Medicinal Chemistry, vol. 35,p. 11–20 (2000).*

TenBrink et al., Annual Reports in Medicinal Chemistry, vol. 29, p. 43–51 (1994).*

* cited by examiner

*Primary Examiner*—Emily Bernhardt
(74) *Attorney, Agent, or Firm*—Finnegan, Henderson, Farabow, Garrett & Dunner L.L.P.

(57) ABSTRACT

The invention relates to novel phenylpiperazine derivatives of the formula wherein: —R represents the group (a) or (b) as indicated in the description. These compounds are (partial) D2 receptor agonists and are usefull for treating CNS disorders, in particular Parkinson's disease.

(I)

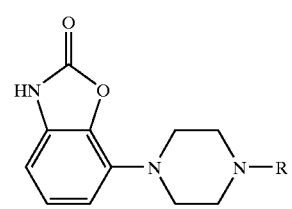

5 Claims, No Drawings

PHENYLPIPERAZINES

The invention relates to novel phenylpiperazine derivatives of the formula (1):

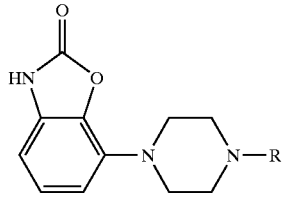
(1)

wherein:
R is a group of the formula (a) or (b)

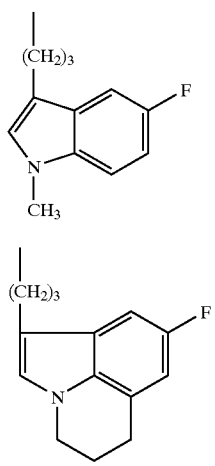

and salts thereof.

It has been found that the compounds according to the invention show high affinity for both the dopamine $D_2$ receptor and the serotonin reuptake site. This combination is useful for the treatment of psychotic disorders like schizophrenia (treating both positive and negative symptoms), and other psychiatric disorders.

The compounds show activity as (partial) agonists which makes them suited as well for the treatment of Parkinson's disease.

The compounds show antagonist activity at dopamine $D_2$ receptors as they antagonize apomorphine-induced climbing behaviour in mice. The compounds also show activity as inhibitors of serotonin reuptake as they potentiate 5-HTP induced behaviour in mice.

The compounds are active in therapeutic models sensitive to clinically relevant antipsychotics (e.g. the conditioned avoidance response; Van der Heyden & Bradford, Behav. Brain Res., 1988, 31:61–67) and antidepressants or anxiolytics (e.g. suppression of stress-induced vocalization; van der Poel et al., Psychopharmacology, 1989, 97: 147–148).

The compounds are active in clinically relevant models for Parkinson's disease (e.g. turning rat behaviour; U. Ungerstedt, Acta Physiol. Scand., 1971, 82 (suppl. 367): 69–93).

In contrast to clinically relevant dopamine $D_2$ receptor antagonists the described compounds have a low propensity to induce catalepsy in rodents and as such are likely to induce less extrapyrimidal side effects than existing antipsychotic agents.

The inhibitory activity of serotonin reuptake inherent in these compounds may be responsible for the therapeutic effects observed in behavioural models sensitive to either antidepressants or anxiolytics.

The compounds can be used for the treatment of affections or diseases of the central nervous system caused by disturbances in either the dopaminergic or serotonergic systems, for example: aggression, anxiety disorders, autism, vertigo, depression, disturbances of cognition or memory, Parkinson's disease and in schizophrenia and other psychotic disorders.

Pharmacologically acceptable acids with which the compounds of the invention can form suitable acid addition salts are for example hydrochloric acid, sulphuric acid, phosphoric acid, nitric acid, and organic acids such as citric acid, fumaric acid, maleic acid, tartaric acid, acetic acid, benzoic acid, p-toluene sulphonic acid, methanesulphonic acid and naphthalene sulphonic acid.

The compounds and their acid addition salts can be brought into forms suitable for administration by means of suitable processes using auxiliary substances such as liquid and solid carrier materials.

The compounds having formula (1) can be prepared by reaction of a compound of the formula

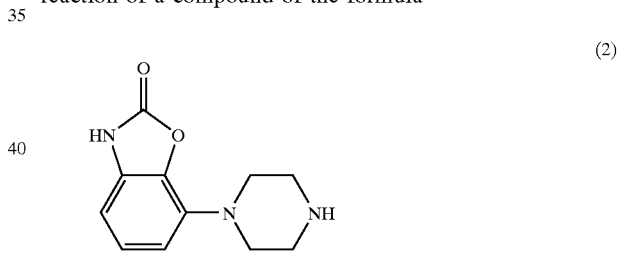
(2)

under basic conditions with a compound of the formula

L–(a) or L–(b)

in which formulae (a) and (b) have the meanings given above, and L is a so-called leaving group such as a halogen atom or a mesylate group.

The piperazine compound having formula (2) can be obtained as described in EP 0189612.

The starting materials of the formula L–(a) can be obtained according to the following scheme:

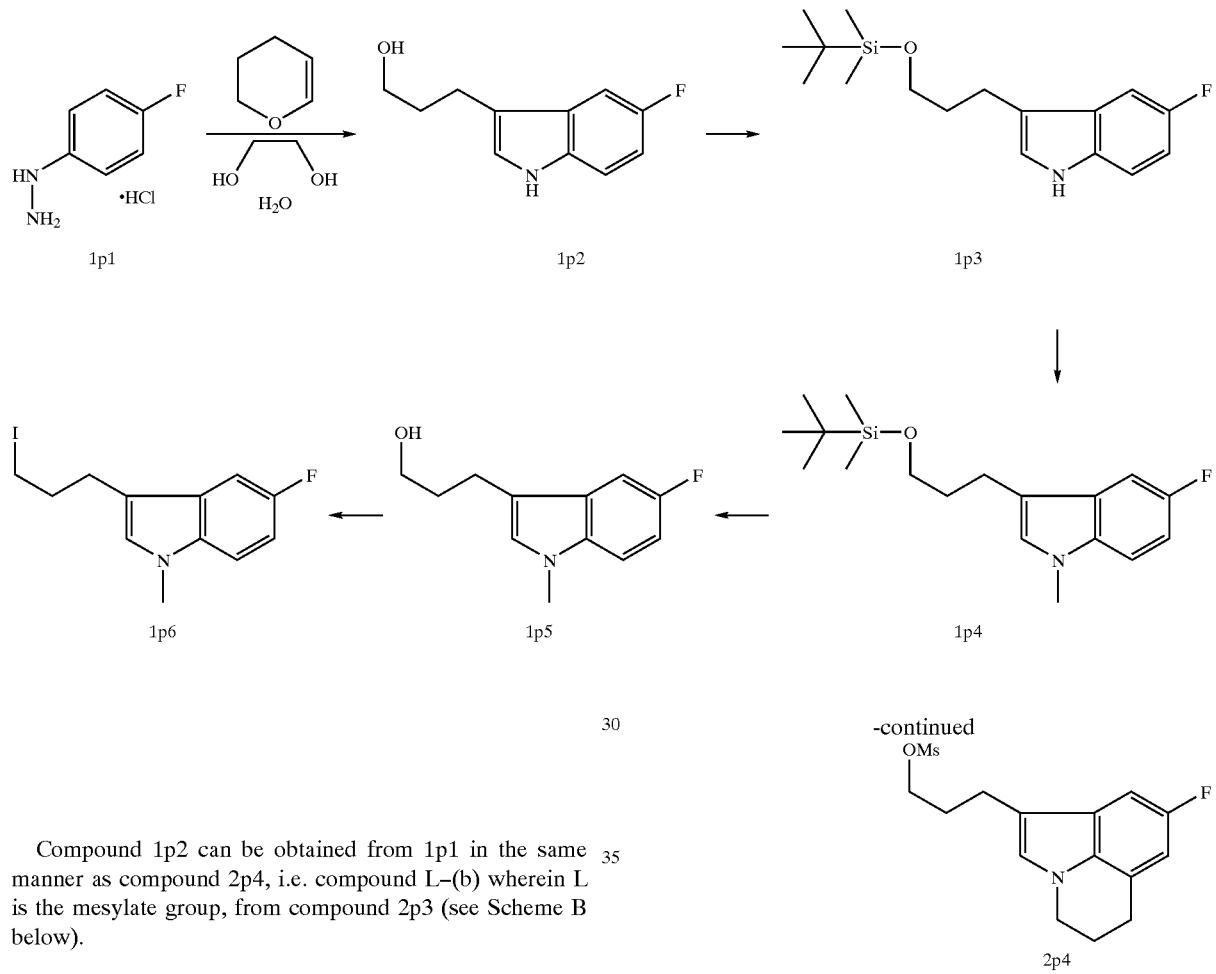

Compound 1p2 can be obtained from 1p1 in the same manner as compound 2p4, i.e. compound L–(b) wherein L is the mesylate group, from compound 2p3 (see Scheme B below).

The invention is illustrated by means of the following Examples.

EXAMPLE 1

18.1 g (0.1 mol) of 2p1 was dissolved in 250 ml of $CH_2Cl_2$ and brought to 0° C. A solution, made from 50 ml of concentrated sulfuric acid poured on 200 g of ice, was added to the $CH_2Cl_2$ solution. The resulting mixture was maintained at 0° C. by applying an ice/acetone cooling bath. To the latter solution, 8.3 g (0.12 mol) of $NaNO_2$ dissolved in 50 ml of water, was added dropwise, while the temperature was kept below 2° C. Stirring was continued for 1 hour. Subsequently, the organic layer was separated, the water layer extracted ($CH_2Cl_2$) once, the combined organic fractions were dried on $MgSO_4$. Removal of the drying agent by filtration and concentration in vacuo of the fillrate yielded 17.8 g (99%) of crude dark yellow 2p2. Under a nitrogen atmosphere, a solution of 17.8 g (0.099 mol) of 2p2 in 100 ml of dry THF was added dropwise very carefully to a suspension of $LiAlH_4$ (9.75 g, 244 mmol) in refluxing dry THF. After the addition was complete, the resulting mixture was allowed to react for another 40 minutes. The reaction mixture was brought to room temperature and further cooled by an ice/ethanol cooling bath. Subsequently were added: 9.75 ml of water/THF (1/1), 18.5 ml of 2N NaOH(aq) and 18.5 ml of water. The resulting mixture was brought to reflux for 20 minutes. After cooling down, the reaction mixture was filtered (Hyflo), the resulting filtrate was concentrated in vacuo, yielding 15.9 g of residue. The latter was dissolved in 98 ml of 1N HCl in EtOAc, the resulting precipitate was filtered yielding 17.5 g (87%) of 2p3.HCl. 17.5 g (86 mmol) of 2p3.HCl were dissolved in a mixture 190 ml of ethyleneglycol and 90 ml of water, the resulting solution was heated to 95° C. Subsequently 7.96 g (94.6 mmol) of (3,4)-dihydro-2H-pyran carefully was added dropwise. After the addition was complete, stirring was continued for 3 hours at 95° C. After the reaction mixture reached room temperature, water and some brine were added and extraction was performed with EtOAc (3×). The combined organic fractions were washed with water, NaHSO$_3$(aq), water, NaHCO$_3$(aq), NaCl(aq) respectively after which the organic fraction was dried on Na$_2$SO$_4$. Removal of the drying agent and solvent yielded a residue which was purified by column chromatogaphy (SiO$_2$, eluent MeOH/CH$_2$Cl$_2$ 3/97), resulting in 12 g (63%) of a dark red oil containing the corresponding alcohol of 2p4 which solidified on standing. Subsequently the alcohol was converted into its mesylate by standard procedures (MsCl, diisopropylethylamine in CH$_2$Cl$_2$, 0° C.) yielding 2p4 (98% yield).

The phenylpiperazine having formula (2) was reacted with 2p4 according to the procedure mentioned in EP 0900792, yielding compound (1) wherein R is the group of formula (b); (m.p.: 182–5° C.).

EXAMPLE 2

1p1 was converted into 1p2 analogously to the preparation of 2p4 (in Example 1). 1p2 was converted into 1p3 (98%) according to the procedure described in RajanBabu et.al., *J. Org. Chem.* 51, (1986), 1704.

Under a nitrogen atmosphere, 31.9 g (103 mmol) of 1p3 were dissolved in 49 ml of DMF. The resulting solution was added slowly to a solution containing 5.88 g (134 mmol, 1.3 eq) of an oily suspension containing 55% of NaH in 148 ml of DMF, after which stirring was continued for one hour at room temperature, after which the reaction mixture was cooled (ice/water). To the latter solution, 8.34 ml (19.02 g, 134 mmol, 1.3 eq) of MeI diluted in 49 ml of DMF, were added dropwise. The reaction mixture was stirred for an additional 16 hours at room temperature. To the latter, water was added and extraction performed; Et$_2$O (2×), the organic fraction was washed with water (2×) and brine (1×), and eventually dried on MgSO$_4$. After removal of the drying agent and solvent in vacuo, the residu was subjected to column chromatography (SiO$_2$, eluent: CH$_2$Cl$_2$/hexane 3/1) yielding 26.2 g (79%) of 1p4 as a yellowish oil.

Under a nitrogen atmosphere, 25.03 g (78 mmol) of 1p4 were dissolved in 110 ml of THF after which 93 ml (0.93 mmol, 1.2 eq.) of 1N (nBut)$_4$N$^+$F$^-$ in THF were added. After one hour of stirring, Et$_2$O was added, and the resulting mixture washed with water (3×) and brine (1×). The organic layer was dried on Na$_2$SO$_4$. After removal of the drying agent and the solvent, the residue was taken up in toluene and subsequently concentrated in vacuo to remove traces of (tert.)butyltrimethylsilylfluoride. The residu was subjected to flashchromatography (SiO$_2$, eluent Et$_2$O), eventually yielding 14.8 g (92%) of 1p5.

1.69 g (6.45 mmol) of PPh$_3$ and 0.44 g (6.44 mmol) of imidazole were dissolved in 20 ml of CH$_2$Cl$_2$, after which 1.64 g (6.45 mmol) of iodine were added portionwise. The reaction mixture was stirred for another 30 minutes at room temperature. To the latter mixture 1.07 g (5.16 mmol) of 1p5 dissolved in 10 ml of CH$_2$Cl$_2$ were added slowly. After 30 minutes the reaction mixture was washed with NaHCO$_3$(aq), NaHSO$_3$(aq) and brine, the remaining organic fraction dried on Na$_2$SO$_4$. After removal of the drying agent and the solvent in vacuo, the residu was dissolved in Et$_2$O, the precipitate which formed (Ph$_3$PO) was removed by filtration. The filtrate was concentrated in vacuo, the residue purified by flash chromatography (SiO$_2$), eluent CH$_2$Cl$_2$/hexane 1/1), yielding 1.45 g (88%) of the desired iodide 1p6.

The phenylpiperazine having formula (2) was reacted with 1p6 according to the procedure described in EP 0900792, yielding compound 1 wherein R is group (a) (m.p.: 202–4° C.).

What is claimed is:
1. A phenylpiperazine derivatives having formula (1)

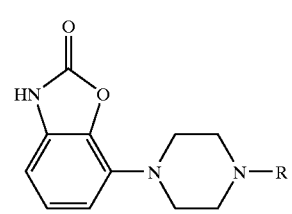

(1)

wherein R is a group of the formula (a) or (b)

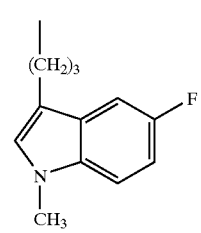

(a)

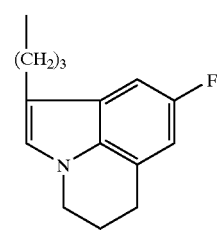

(b)

or a salt thereof.

2. Method for the preparation of a phenylpiperazine derivatives or a salt thereof as claimed in claim 1, comprising reacting a compound having formula (2)

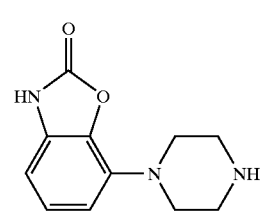

(2)

under basic conditions with a compound of the formula

L-(a) or L-(b)

in which formula L is a leaving group and (a) and (b) have the meaning given in claim 1, to yield the phenylpiperazine derivatives or salt thereof.

3. A pharmaceutical composition comprising at least one phenylpiperazine derivatives or salt thereof as claimed in claim 1, or a combination thereof, and at least one auxiliary substance.

4. A method of treating Parkinson's Disease in a human or animal patient in need of such treating, comprising administering to the patient an efficacious amount of at least one phenylpiperazine derivatives or at least one salt thereof as claimed in claim 1, or a combination thereof.

5. A method of treating schizophrenia, anxiety, or depression, or a combination of two or more of the foregoing, in a human or animal patient in need of such treating, comprising administering to the patient an efficacious amount of at least one phenylpiperazine derivatives or at least one salt thereof as claimed in claim 1, or a combination thereof.

* * * * *

UNITED STATES PATENT AND TRADEMARK OFFICE
CERTIFICATE OF CORRECTION

PATENT NO. : 6,828,325 B2
DATED : December 7, 2004
INVENTOR(S) : Roelof W. Feenstra et al.

It is certified that error appears in the above-identified patent and that said Letters Patent is hereby corrected as shown below:

Title page,
Item [57], ABSTRACT,
Line 4, "usefull" should read -- useful --.

Column 6,
Lines 13, 48 and 67, "derivatives" should read -- derivative --.

Column 7,
Line 2, "derivatives" should read -- derivative --.
Line 2, "or salt" should read -- or at least one salt --.

Signed and Sealed this

Twenty-second Day of February, 2005

JON W. DUDAS
*Director of the United States Patent and Trademark Office*